US007819900B2

(12) United States Patent  
Parsons

(10) Patent No.: US 7,819,900 B2
(45) Date of Patent: Oct. 26, 2010

(54) TRI-JOINT IMPLANT METHODS

(75) Inventor: Matthew Parsons, Fall River, MA (US)

(73) Assignee: DePuy Spine, Inc., Raynham, MA (US)

( * ) Notice: Subject to any disclaimer, the term of this patent is extended or adjusted under 35 U.S.C. 154(b) by 1583 days.

(21) Appl. No.: 10/908,055

(22) Filed: Apr. 26, 2005

(65) Prior Publication Data

US 2005/0277938 A1  Dec. 15, 2005

Related U.S. Application Data

(60) Provisional application No. 60/575,017, filed on May 27, 2004.

(51) Int. Cl.
A61B 17/70 (2006.01)
(52) U.S. Cl. .............. 606/247; 606/248; 623/17.11; 623/17.15
(58) Field of Classification Search ... 623/17.11–17.15; 606/247, 248
See application file for complete search history.

(56) References Cited

U.S. PATENT DOCUMENTS

| | | | |
|---|---|---|---|
| 3,919,772 A | 11/1975 | Lenczycki | |
| 4,743,260 A | 5/1988 | Burton | |
| 4,759,769 A | 7/1988 | Hedman et al. | |
| 4,997,432 A | 3/1991 | Keller | |
| 5,092,866 A | 3/1992 | Breard | |
| 5,122,130 A | 6/1992 | Keller | |
| 5,282,863 A | 2/1994 | Burton | |
| 5,387,213 A | 2/1995 | Breard | |
| 5,415,661 A | 5/1995 | Holmes | |
| 5,474,086 A | 12/1995 | McCormick | |
| 5,531,747 A | 7/1996 | Ray | |
| 5,540,688 A | 7/1996 | Navas | |
| 5,556,431 A | 9/1996 | Buttner-Janz | |
| 5,562,737 A | 10/1996 | Graf | |
| 5,571,191 A | 11/1996 | Fitz | |
| 5,595,563 A * | 1/1997 | Moisdon | 600/12 |
| 5,672,175 A | 9/1997 | Martin | |
| 5,865,846 A | 2/1999 | Bryan et al. | |

(Continued)

FOREIGN PATENT DOCUMENTS

EP  0669109  8/1995

(Continued)

OTHER PUBLICATIONS

Office Action dated Nov. 1, 2007 for U.S. Appl. No. 10/908,054.

Primary Examiner—Thomas C Barrett
Assistant Examiner—David W Bates
(74) Attorney, Agent, or Firm—Nutter McClennen & Fish LLP

(57) ABSTRACT

Methods and devices are provided for replacing damaged, injured, diseased, or otherwise unhealthy elements of the spinal three-joint complex, such as the facet joints and discs. In one exemplary embodiment, a joint replacement system includes a facet replacement component that is adapted to replace and/or augment the facet joints, and a disc replacement component that is adapted to replace a spinal disc. The facet replacement component and the disc replacement component can couple to one another to allow and/or control flexion, extension, and/or lateral bending of the spine, preferably while substantially restricting posterior-anterior shear and axial rotation of the spine.

20 Claims, 11 Drawing Sheets

U.S. PATENT DOCUMENTS

| | | |
|---|---|---|
| RE36,221 E | 6/1999 | Breard |
| 5,961,516 A | 10/1999 | Graf |
| RE36,758 E | 6/2000 | Fitz |
| 6,132,464 A | 10/2000 | Martin |
| 6,267,764 B1 | 7/2001 | Elberg |
| 6,273,888 B1 | 8/2001 | Justis |
| 6,416,551 B1 | 7/2002 | Keller |
| 6,419,703 B1 | 7/2002 | Fallin |
| 6,554,831 B1 | 4/2003 | Rivard |
| 6,565,605 B2 | 5/2003 | Goble |
| 6,579,319 B2 | 6/2003 | Goble |
| 6,610,091 B1 | 8/2003 | Reiley |
| 6,645,207 B2 | 11/2003 | Dixon |
| 6,669,729 B2 | 12/2003 | Chin |
| 6,811,567 B2 | 11/2004 | Reiley |
| 6,896,676 B2 | 5/2005 | Zubok et al. |
| 6,908,484 B2 | 6/2005 | Zubok et al. |
| 2002/0065557 A1 | 5/2002 | Goble |
| 2002/0072800 A1 | 6/2002 | Goble |
| 2002/0123806 A1 | 9/2002 | Reiley |
| 2002/0133155 A1 | 9/2002 | Ferree |
| 2003/0004572 A1 | 1/2003 | Goble |
| 2003/0028250 A1 * | 2/2003 | Reiley et al. .............. 623/17.11 |
| 2003/0055427 A1 | 3/2003 | Graf |
| 2003/0083657 A1 | 5/2003 | Drewry |
| 2003/0109880 A1 | 6/2003 | Shirado |
| 2003/0135277 A1 | 7/2003 | Bryan et al. |
| 2003/0153912 A1 | 8/2003 | Graf |
| 2003/0171749 A1 | 9/2003 | Le Couedic |
| 2003/0171750 A1 | 9/2003 | Chin |
| 2003/0191470 A1 | 10/2003 | Ritland |
| 2003/0191532 A1 | 10/2003 | Goble |
| 2003/0199981 A1 | 10/2003 | Ferree |
| 2003/0220642 A1 | 11/2003 | Freudiger |
| 2003/0220643 A1 | 11/2003 | Ferree |
| 2004/0002708 A1 | 1/2004 | Ritland |
| 2004/0006391 A1 | 1/2004 | Reiley |
| 2004/0049189 A1 | 3/2004 | Le Couedic |
| 2004/0049190 A1 | 3/2004 | Biedermann |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0073215 A1 | 4/2004 | Carli |
| 2004/0111154 A1 | 6/2004 | Reiley |
| 2004/0116927 A1 | 6/2004 | Graf |
| 2004/0143264 A1 | 7/2004 | McAfee |
| 2004/0176852 A1 | 9/2004 | Zubok et al. |
| 2004/0186475 A1 | 9/2004 | Falahee |
| 2004/0236329 A1 | 11/2004 | Panjabi |
| 2005/0033431 A1 | 2/2005 | Gordon et al. |
| 2005/0101954 A1 | 5/2005 | Simonson |
| 2005/0101956 A1 | 5/2005 | Simonson |
| 2005/0113924 A1 | 5/2005 | Buttermann |
| 2005/0154465 A1 | 7/2005 | Hodges et al. |
| 2005/0171610 A1 * | 8/2005 | Humphreys et al. ...... 623/17.15 |

FOREIGN PATENT DOCUMENTS

| | | |
|---|---|---|
| FR | 2775587 A1 | 9/1999 |
| FR | 2822674 A1 | 10/2002 |
| WO | WO 01/45576 | 6/2001 |
| WO | WO 02/17803 | 3/2002 |
| WO | WO 02/43603 | 6/2002 |
| WO | WO 02/102259 | 12/2002 |
| WO | WO 03/007828 | 1/2003 |
| WO | WO 03/009737 | 2/2003 |
| WO | WO 2004/024011 | 3/2004 |
| WO | WO 2004/034916 | 4/2004 |
| WO | 2005110292 A2 | 11/2005 |

* cited by examiner

TRI-JOINT IMPLANT METHODS

CROSS REFERENCE TO RELATED APPLICATIONS

The pending application claims priority to U.S. Provisional Application Ser. No. 60/575,017, filed May 27, 2004, and entitled "Tri-Joint (Disc and Facet) Implant," which is hereby incorporated by reference in its entirety.

BACKGROUND OF THE INVENTION

The vertebrae in a patient's spinal column are linked to one another by the disc and the facet joints, which control movement of the vertebrae. Each vertebra has a pair of articulating surfaces located on the left side, and a pair of articulating surfaces located on the right side, and each pair includes a superior articular surface, which faces upward, and an inferior articular surface, which faces downward. Together the superior and inferior articular surfaces of adjacent vertebra form a facet joint. Facet joints are synovial joints, which means that each joint is surrounded by a capsule of connective tissue and produces a fluid to nourish and lubricate the joint. The joint surfaces are coated with cartilage allowing the joints to move or articulate relative to one another. In combination with the intervertebral disc, the two facet joints form the spinal three-joint complex.

Diseased, degenerated, impaired, or otherwise painful facet joints and/or discs can require surgery to relieve pain or restore function to the three-joint complex. Subsequent surgery may also be required after a laminectomy, as a laminectomy predisposes the patient to instability and may lead to post-laminectomy kyphosis (abnormal forward curvature of the spine), pain, and neurological dysfunction. Current clinical data have suggested that degeneration of one member of the three joint complex, that is either the discs or the facet joints, contributes to the degeneration of the other. While implants are available for replacing either a diseased disc or the facet joints, there are no implants that can be used to replace the entire spinal three-joint complex.

Accordingly, there remains a need for improved systems and methods for repairing and/or replacing the spinal three-joint complex.

BRIEF SUMMARY OF THE INVENTION

Disclosed herein are various methods and devices for repairing and/or replacing a damaged facet joint, and optionally other elements of a patient's spine, such as the disc. In one exemplary embodiment, a facet replacement device for dynamically stabilizing the spine is provided having a first member that is adapted to couple to a first vertebra and a second member that is adapted to couple to a second vertebra adjacent to the first vertebra. The second member can be in communication with the first member to control movement of the first and second vertebrae relative to one another. The facet replacement device can also include a connector that is adapted to couple the first and/or second member to a disc replacement device that is disposed between the first and second vertebrae.

The first and second members can have a variety of configurations, but in one exemplary embodiment the first and second members are in the form of plates that are adapted to attach to a posterior surface of a vertebra. One or more thru-bores can be formed therein for receiving a fastening element, such as a bone screw, for mating the members to a vertebra. Each plate can have a variety of shapes and sizes, but in one exemplary embodiment the plates are curved to match a contour of a posterior surface of a vertebra. The plates can also have a shape that avoids contact with the spinous process. Furthermore, the plates can be plastically deformed in situ, such that the curvature of the plates can be manipulated by the surgeon during the surgery to fit the specific anatomy of each patient, in the same manner that cervical plates and lumbar rods are bent to match patient anatomy during a fusion procedure.

The first and second members can also be adapted to control movement of the adjacent vertebrae relative to one another. In one embodiment, the first and second members can be integrally formed with one another or mated to one another to either prevent or limit movement of the adjacent vertebrae relative to one another. For example, the first and second members can include a flexible connection formed there between, or at least a portion of the first and second members can be formed from a flexible material to allow limited movement of the vertebrae. In another embodiment, the first and second members can be formed from separate pieces that are adapted to move relative to one another. In one exemplary embodiment, the first and second members can include one or more bearing surfaces formed thereon and adapted to move against one another to allow the first and second members to articulate relative to each other. While the bearing surfaces can have a variety of configurations, in one exemplary embodiment the bearing surfaces can be in the form of fins that are configured to slide against one another. In certain exemplary embodiments, the fins can be configured to allow flexion while limiting or preventing extension, axial rotation, and/or lateral bending of the adjacent vertebrae. For example, the first member can have one or more longitudinally extending fins with an outwardly facing bearing surface formed thereon, and the second member can have one or more angled fins with an inwardly facing bearing surface formed thereon. The fins can be positioned such that the outwardly facing bearing surface(s) of the first member slides against the inwardly facing bearing surface(s) of the second member to allow flexion while limiting or preventing extension, axial rotation, and/or lateral bending of the adjacent vertebrae.

In another exemplary embodiment, as noted above, the first and second members can include connectors for mating to a disc replacement device disposed between the adjacent vertebrae. While the connectors can have a variety of configurations, in one exemplary embodiment the connectors can be in the form of elongate members that include a mating feature, such as threads, formed on a portion thereof for mating with a corresponding mating feature formed on or in the disc replacement member. The first and second members can include thru-bores formed therein for receiving connectors.

In another aspect, a joint replacement system is provided that includes a disc replacement member that is adapted to be disposed between a superior vertebra and an adjacent inferior vertebra, and superior and inferior facet replacement components that are adapted to couple to the superior and inferior vertebra. The disc replacement member can consist of one or more components. At least one of the superior and inferior facet replacement components can be adapted to couple to the disc replacement member. In one exemplary embodiment, the superior facet replacement component includes at least one connector that is adapted to mate to a superior portion of the disc replacement component, and the inferior facet replacement component includes at least one connector that is adapted to mate to an inferior portion of the disc replacement component.

Exemplary methods for dynamically stabilizing the posterior elements of adjacent vertebrae are also disclosed. In one embodiment, the method can include coupling superior and inferior facet replacement members to adjacent superior and inferior vertebrae. In an exemplary embodiment, the superior and inferior replacement members are positioned on a posterior surface of the superior and inferior vertebrae. A fastening element can be inserted through one or more thru-bores formed in each member to attach the facet replacement members to the vertebrae. The method can also include coupling at least one of the superior and inferior facet replacement members to a disc replacement member that is disposed between the adjacent superior and inferior vertebrae.

In other aspects, the method can include adjusting a position of the disc replacement member between the adjacent vertebrae using one or more connectors that couple the superior and/or inferior facet replacement member to the disc replacement member. In one exemplary embodiment, the connector(s) can be in the form of an elongate member having threads formed thereon for engaging corresponding threads formed on or in the disc replacement member, and the connector(s) can be rotated to move the disc replacement device closer to or farther away from the facet replacement members.

In another exemplary embodiment, a method for replacing the spinal three-joint complex is provided and includes replacing a disc disposed between superior and inferior vertebrae with a disc replacement member, attaching opposed lateral portions of a superior facet replacement member to opposed pedicles on the superior vertebra, attaching opposed lateral portions of an inferior facet replacement member to opposed pedicles on the inferior vertebra, and coupling at least one of the superior and inferior facet replacement members to the disc replacement member.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1:
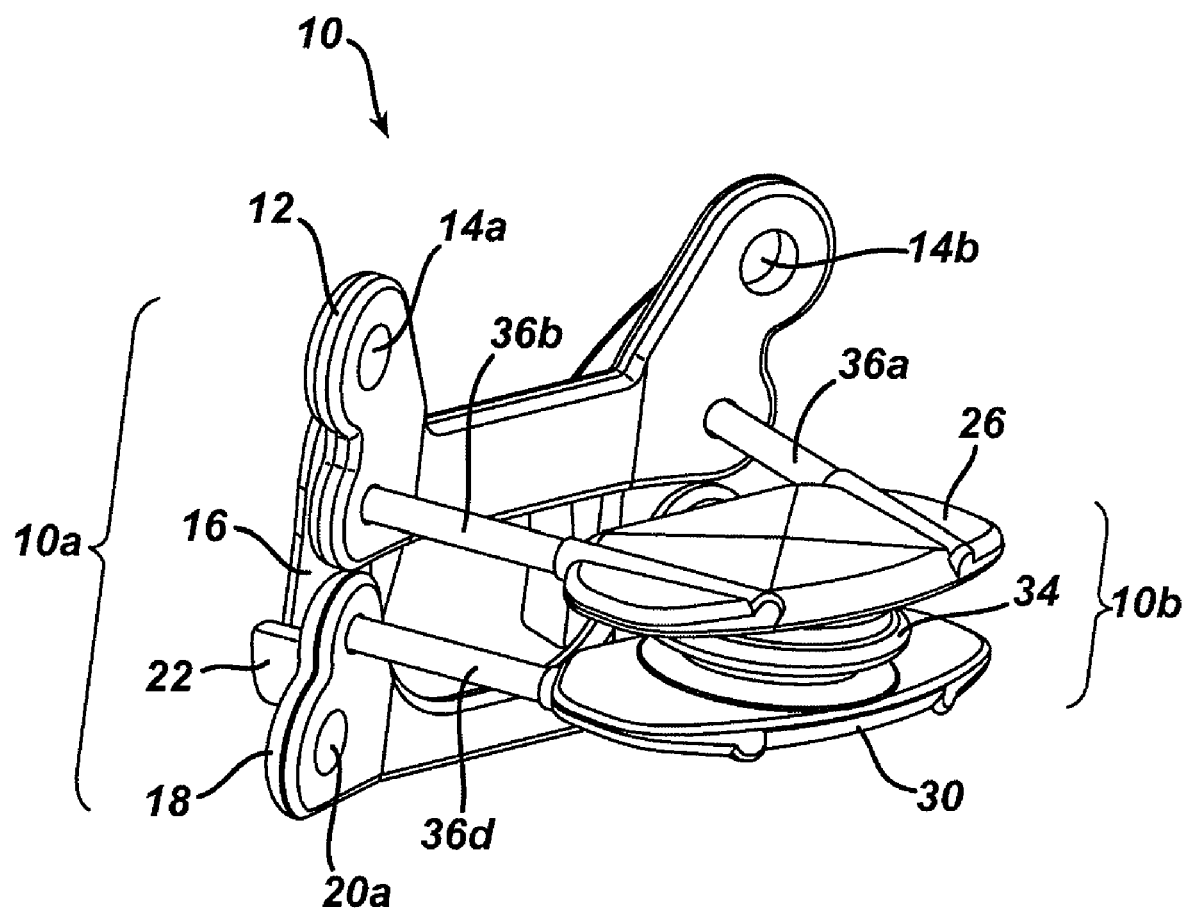
FIG. 1 is an anterior perspective view of one exemplary embodiment of a joint replacement system having a facet replacement component and a disc replacement component.

Disclosed herein are various methods and devices for replacing damaged, injured, diseased, or otherwise unhealthy elements of the spinal three-joint complex, such as the facet joints and discs. FIG. 1 illustrates one exemplary embodiment of a joint replacement system 10 that includes a facet replacement component 10a that is adapted to replace and/or augment the facet joints, and a disc replacement component 10b that is adapted to replace a spinal disc. The facet replacement component 10a and the disc replacement component 10b can couple to one another to allow and/or control flexion, extension, and/or lateral bending of the spine, preferably while substantially restricting posterior-anterior shear and rotation of the spine. A person skilled in the art will appreciate that, while the methods and devices are especially configured for use in restoring and/or replacing the facet joints and disc of a patient's spine by a posterior surgical approach, the methods and devices can be adapted for use in an anterior approach, or they can be used for a variety of other purposes in a variety of other surgical procedures. Moreover, while the methods and devices are described in conjunction with a disc replacement component 10b having a particular configuration, a person skilled in the art will appreciate that the methods and devices can be adapted for use with a variety of spinal prostheses having a variety of other configurations, or it can be adapted for use alone with the natural disc.

Figure 2:
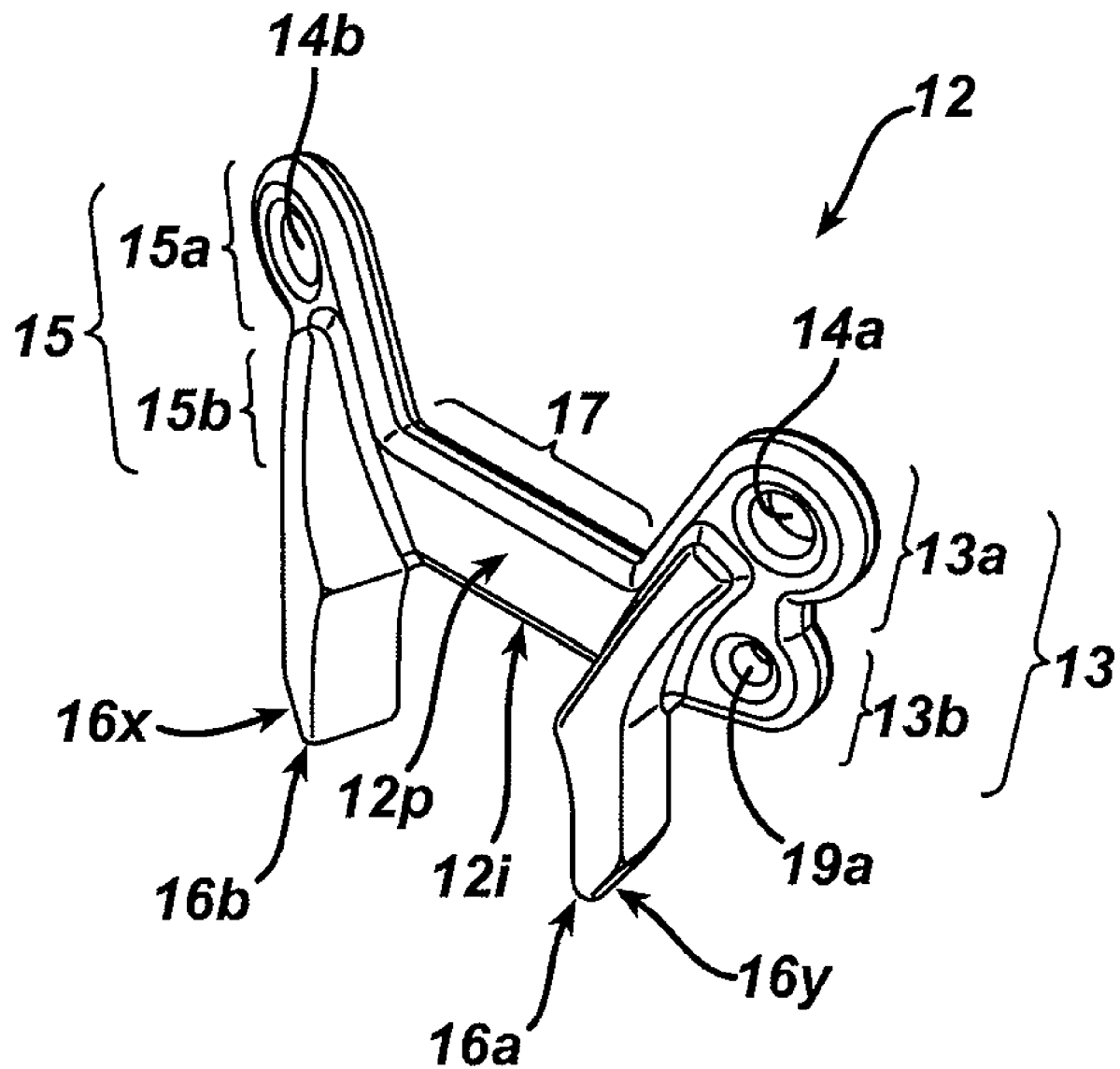
FIG. 2 is a posterior perspective view of a first member of the facet replacement component of the joint replacement system shown in FIG. 1.
Figure 3:
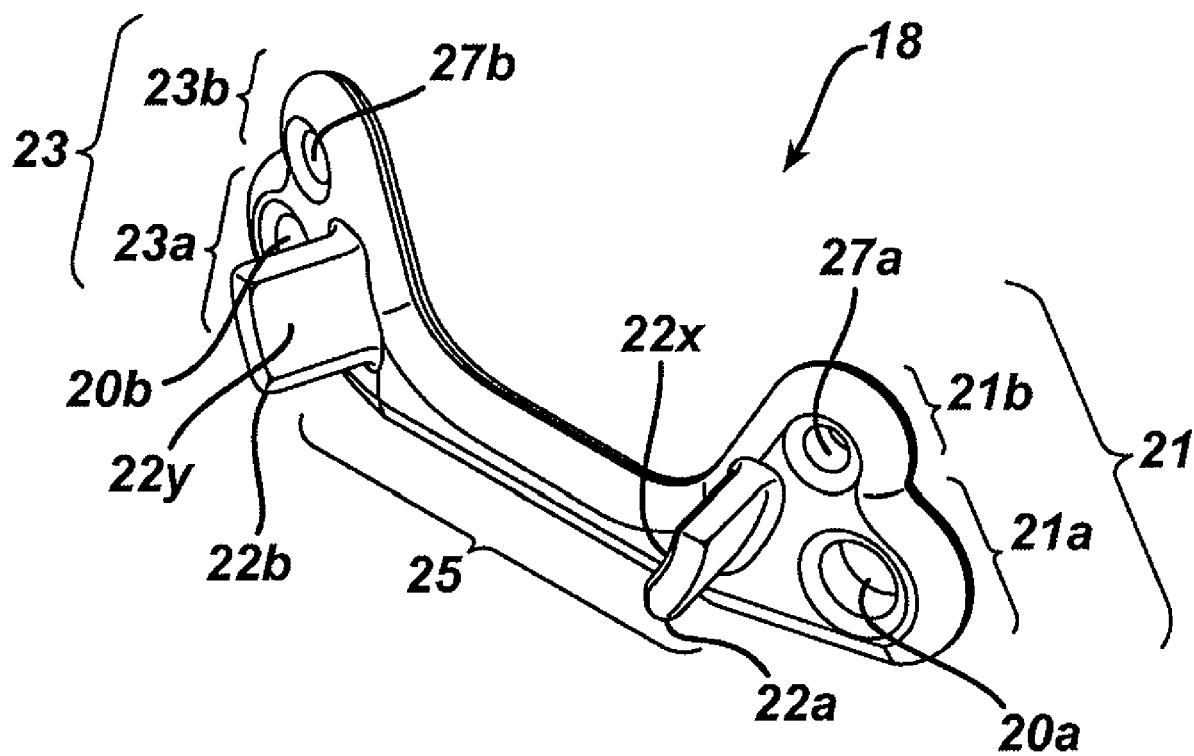
FIG. 3 is a posterior perspective view of a second member of the facet replacement component of the joint replacement system shown in FIG. 1.
Figure 4:
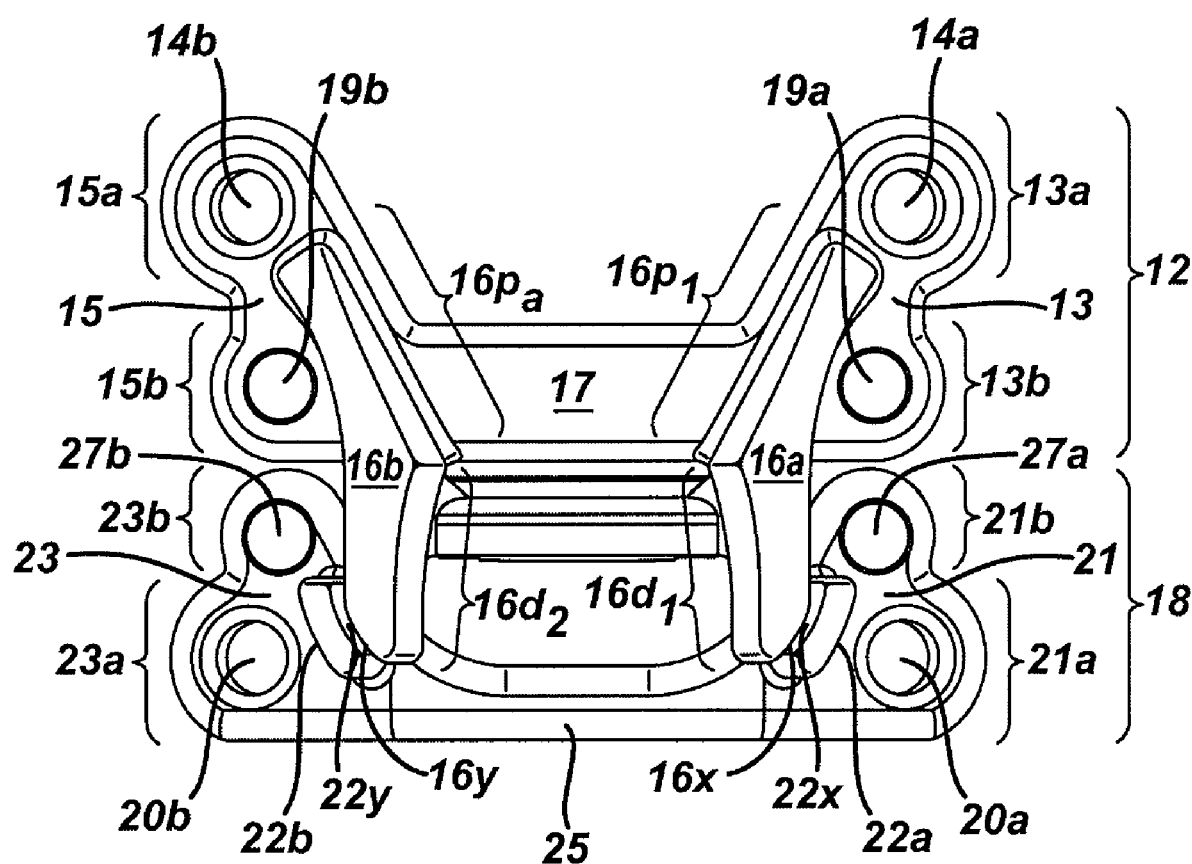
FIG. 4 is a posterior view of the joint replacement system shown in FIG. 1.

FIGS. 2-4 illustrate the facet replacement component 10a in more detail, and as shown, the facet replacement component 10a can include a first or superior member 12 that is adapted to couple to a superior vertebra, and a second or inferior member 18 that is adapted to couple to an inferior vertebra. In use, the first and second members 12, 18 can communicate with one another to control movement of the superior and inferior vertebrae relative to one another. The first and/or second members 12, 18 can also be adapted to couple to a disc replacement component 10b, as will be discussed in more detail below.

The first member 12, shown in more detail in FIG. 2, can have a variety of shapes and sizes, but in one exemplary embodiment the first member 12 can have a shape that complements a shape of the posterior surface of a vertebra. For example, the first member 12 can be in the form of a plate having a curved configuration. The first member 12 can also have a shape that is adapted to avoid contact with the spinous process. In the illustrated exemplary embodiment, the first member 12 has a central elongate portion 17 with a wing-shaped portion 13, 15 formed on each end of the central elongate portion 17. The wing-shaped portions 13, 15 are shown extending in a superior direction from the elongate central portion 17. Such a configuration allows the central elongate portion 17 to be positioned just inferior to the spinous process on a superior vertebra, while allowing the wing-shaped portions 13, 15 to extend in a superior direction around opposed sides of the spinous process. The also facilitates mating of the first member 12 to the vertebra, as the wing-shaped portions 13, 15 can be positioned adjacent to the pedicles of the vertebra for receiving one or more fastening elements adapted to mate the first member 12 to the vertebra, as will be discussed in more detail below.

The second member 18, shown in more detail in FIG. 3, can also have a variety of shapes and sizes, but in an exemplary embodiment it has a shape that is similar to the shape of the first member 12. That is, the second member 18 can also be in the form of a curved plate having a central elongate portion 25 with wing-shaped portions 21, 23 formed on each end of the central elongate portion 25. The wing-shaped portions 21, 23 of the second member 18 can extend in a superior direction to allow the second member 18 to mate to a disc replacement device, as will be described in more detail below. However, such a configuration is not necessary to avoid contact with the spinous process of an inferior vertebra, as the central elongate portion 25 can be positioned superior to the spinous process of the inferior vertebra to allow the wing-shaped portions 21, 23 to mate to the pedicles of the inferior vertebra.

As noted above, the first and second members 12, 18 are adapted to be coupled to the superior and inferior vertebrae. Accordingly, a variety of techniques can be used to attach the first and second members 12, 18 to the vertebrae. In one exemplary embodiment, the first and second members 12, 18 can each include one or more thru-bores formed therein for receiving one or more fastening elements, such as bone screws. As shown in FIGS. 2-3, each wing-shaped portion 13, 15, 21, 23 has a thru-bore 14a, 14b, 20a, 20b formed therein for receiving a fastening element therethrough. The thru-bores 14a, 14b in the first member 12 are formed in a superior region 13a, 15a of the wing-shaped portions 13, 15 to allow the wing-shaped portions 13, 15 to be attached to the pedicles of a superior vertebra. The thru-bores 20a, 20b in the second member 18 are formed in an inferior portion 21a, 23a of the wing-shaped portions 21, 23 to allow the wing-shaped portions 21, 23 to be attached to the pedicles of an inferior vertebra. One skilled in the art will appreciate that the thru-bores 14a, 14b, 20a, 20b can have any configuration that allows them to receive a fastening element, and the configuration can vary depending on the type of fastening element used. In the illustrated embodiment, the thru-bores 14a, 14b, 20a, 20b are substantially circular for receiving a bone screw therethrough. In one exemplary embodiment, these thru-bores 14a, 14b, 20a, 20b can incorporate a polyaxial mechanism of the type commonly used in pedicle screw systems that allows for intra-operative adjustment of bone screw angulation. Other fastening elements include, by way of non-limiting example, rivets, hooks, wires, etc.

As previously indicated, the first and second members 12, 18 can also be adapted to communicate with one another to control movement of the adjacent vertebrae relative to one another. The exemplary embodiment can employ protrusions, or fins, that are positioned and geometrically configured to mimics the natural facet joints. In one exemplary embodiment, as shown in FIGS. 1-4, the first and second members 12, 18 can articulate with one another. While a variety of techniques can be used to allow articulation, in one embodiment each member 12, 18 has two fins 16a, 16b, 22a, 22b formed on and protruding from a posterior surface 12p, 18p thereof for allowing the members 12, 18 to articulate relative to one another. The fins 16a, 16b, 22a, 22b can be positioned at a variety of locations on the first and second members 12, 18, however in the illustrated exemplary embodiment the fins 16a, 16b, 22a, 22b are positioned on the wing-shaped portions 13, 15, 21, 23 just outward of the central portion 17, 25. The fins 16a, 16b, 22a, 22b can also be formed inward of thru-bores 14a, 14b, 20a, 20b formed in the wing-shaped portions 13, 15, 21, 23. The shape of the fins 16a, 16b, 22a, 22b can also vary, but in one exemplary embodiment the fins 16a, 16b on the first member 12 have an elongate shape with proximal portions $16p_1$, $16p_2$ that converge in an inferior direction, and distal portions $16d_1$, $16d_2$ that are substantially parallel to one another, and the fins 22a, 22b on the second member 18 have a substantially rectangular cross-sectional shape. The fins 16a, 16b on the first member 12 can also extend in an inferior direction beyond an inferior edge 12i of the first member 12. This allows the fins 16a, 16b on the first member 12 to extend toward and bear against the fins 22a, 22b on the second member 18.

Each fin 16a, 16b, 22a, 22b can also include a bearing surface 16x, 16y, 22x, 22y formed thereon for slidably bearing against one another. In the illustrated exemplary embodiment, bearing surfaces 16x, 16y are formed on an outwardly-facing surface of the distal portions $16d_1$, $16d_2$ of the first member 12, and bearing surfaces 22x, 22y are formed on an inwardly-facing surface of the fins 22a, 22b of the second member 18. Each bearing surface 16x, 16y, 22x, 22y can also vary in shape and size, but in one exemplary embodiment the bearing surfaces 16x, 16y, 22x, 22y have complementary shapes. For example, the bearing surfaces 16x, 16y on the first member 12 can have a convex shape and the bearing surfaces 22x, 22y on the second member 18 can have a concave shape for slidably seating the convex bearing surfaces 16x, 16y of the first member 12. This exemplary embodiment can mimic the bearing surface orientation of the lumbar facets.

In use, the configuration of the bearing surfaces 16x, 16y, 22x, 22y can be effective to control flexion, extension, axial rotation, and/or lateral bending of the adjacent vertebrae. For example, the angle of the fins 16a, 16b, 22a, 22b and/or the bearing surfaces 16x, 16y, 22x, 22y on the first and/or second members 12, 18 can be adapted to limit extension and/or lateral bending of the adjacent vertebrae relative to one another. As shown in FIG. 4, the fins 22a, 22b on the second member 18 converge in an inferior direction, and the bearing surfaces 16x, 16y on the first member 12 converge in an inferior direction. As a result, when the fins 16a, 16b on the first member 12 are slid in an inferior direction relative to the fins 22a, 22b on the second member 18, the angle of the fins 22a, 22b on the second member 18 will eventually engage the fins 16a, 16b on the first member 12 to prevent further inferior movement of the first member 12 relative to the second member 18, in turn limiting extension of the adjacent vertebrae relative to one another. The angle of the fins 22a, 22b on the second member 18 can also limit or prevent lateral bending and/or axial rotation, as the fins 22a, 22b will also engage the fins 16a, 16b on the first member 12 to limit or prevent relative lateral movement thereof. The fins 16a, 16b, 22a, 22b on the first and second members 12, 18 are also particularly advantageous in that they can prevent antero-posterior translation and shearing of the vertebrae relative to one another.

Figure 5:
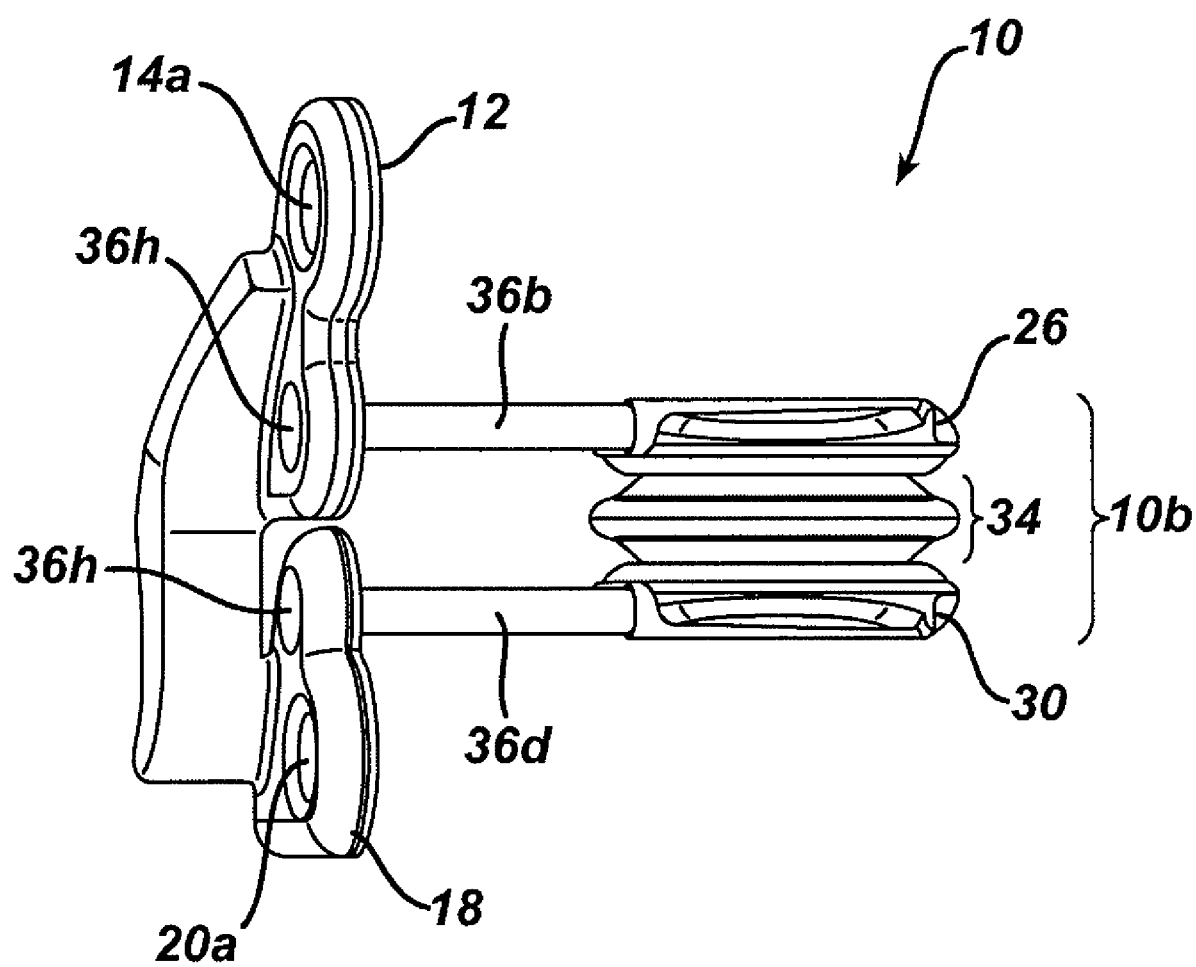
FIG. 5 is a posterior view of another embodiment of a joint replacement system.

A person skilled in the art will appreciate that a variety of other techniques can be used to control movement of two adjacent vertebrae relative to one another. For example, the fins 22a, 22b on the second member 18 can have one or more grooves formed therein for slidably receiving the fins 16a, 16b on the first member 12. The fins 22a, 22b on the second member 18 can, in other embodiments, include a stop formed thereon to limit movement of the first member 12 relative thereto. The stop, or all or some of the fins 16a, 16b, 22a, 22b themselves, could be formed from a flexible material to provide some shock absorption between the two members 12, 18. In other aspects, the fins 16a, 16b, 22a, 22b can be fixedly mated or integrally formed with one another. For example, a mating element, such as a pin, could be inserted through a portion of each fin 16a, 16b, 22a, 22b to mate the fins 16a, 16b on the first member 12 to the fins 22a, 22b on the second member 18, thereby preventing movement of the first and second members 12, 18 relative to one another. Alternatively, as shown in FIG. 5, the first and second members 12', 18' can be connected by a flexible member 100' that allows some movement between the first and second members 12', 18'. In other embodiments, the fins 16a, 16b, 22a, 22b can be rigid or flexible (or elastic) depending upon the needs of the surgeon, the later being particularly advantageous if the fins 16, 22 are mated together.

A person skilled in the art will also appreciate that the materials used to form the fins 16a, 16b, 22a, 22b can vary depending on the configuration of the fins 16a, 16b, 22a, 22b, and that a variety of materials can be used. Suitable exemplary materials for forming the fins 16a, 16b, 22a, 22b include, by way of non-limiting example, titanium, stainless steel, cobalt chrome, plastics such as polyethylene, polyurethane, PEEK, silicone, and polyurethane polycarbonate, and various ceramics, or composite combinations thereof. In other embodiments, the bearing surfaces 16x, 16y, 22x, 22y on the fins 16a, 16b, 22a, 22b can be coated with a material that is adapted to reduce friction and wear on the bearing surfaces 16x, 16y, 22x, 22y. Suitable exemplary coatings include, by way of non-limiting example, titanium nitride (TiN), titanium carbide, chromium carbide, pyrolytic carbon, diamond-like carbon, and other similar materials.

In another exemplary embodiment, as previously noted, the first and/or second members 12, 18 of the facet replacement device 10a can be adapted to mate with a disc replacement device 10b disposed between adjacent vertebrae. A variety of techniques can be used to mate the facet replacement device 10a to the disc replacement device 10b, but in one exemplary embodiment the first and second members 12, 18 can each include one or more openings formed therein for receiving a connector. As shown in FIGS. 2-4, each wing-shaped portion 13, 15 on the first member 12 has an opening 19a, 19b formed in an inferior region 13b, 15b (which can also be considered to be a terminal end of the elongate central portion 17) for receiving a connector. As is further shown, each wing-shaped portion 21, 23 on the second member 18 has an opening 27a, 27b formed in a superior region 21b, 23b thereof for receiving a connector. The shape and size of each opening 19a, 19b, 27a, 27b can vary depending on the shape and size of the connectors, however in the illustrated exemplary embodiment each opening 19a, 19b, 27a, 27b is substantially circular and polyaxial, to allow the angle of the connector to vary depending on patient anatomy.

Figure 7:
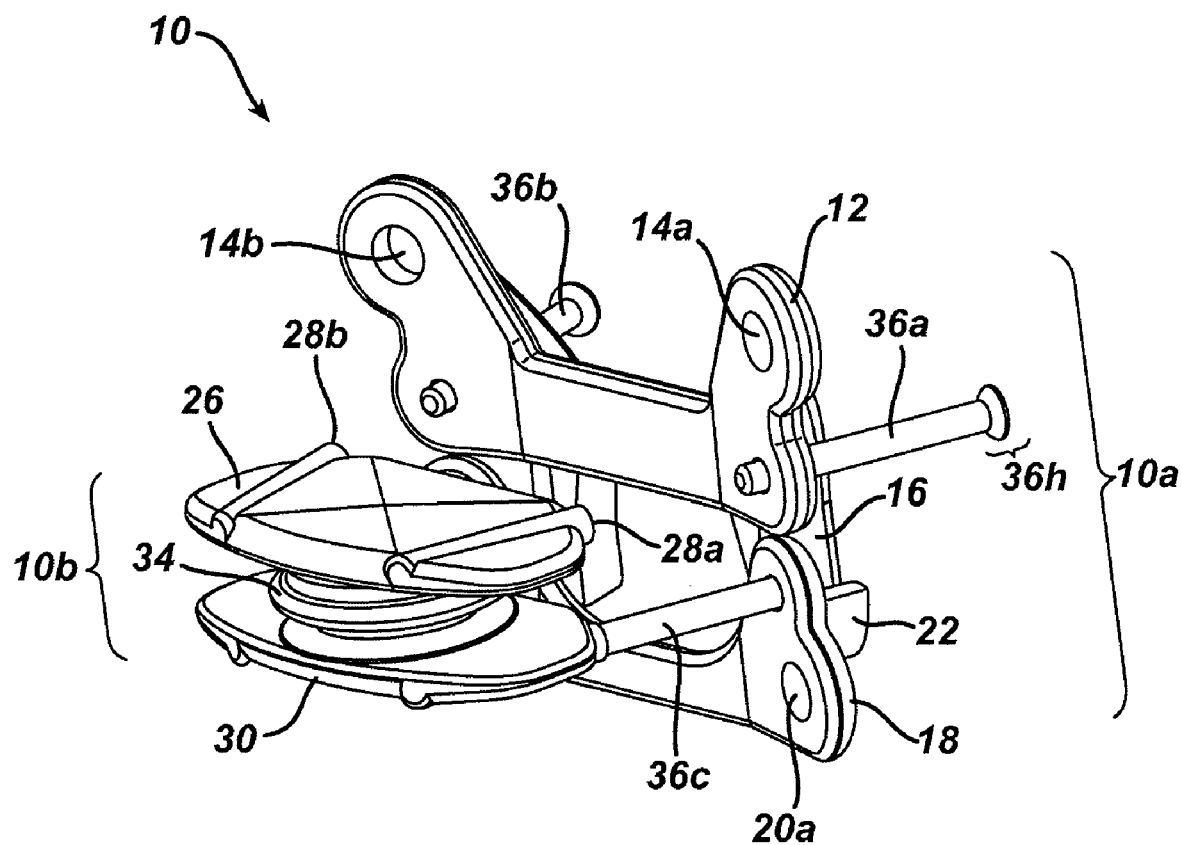
FIG. 7 is an anterior perspective view of the disc replacement component shown in FIGS. 6A and 6B being mated to the first and second facet replacement members shown in FIGS. 2-4.
Figure 8:
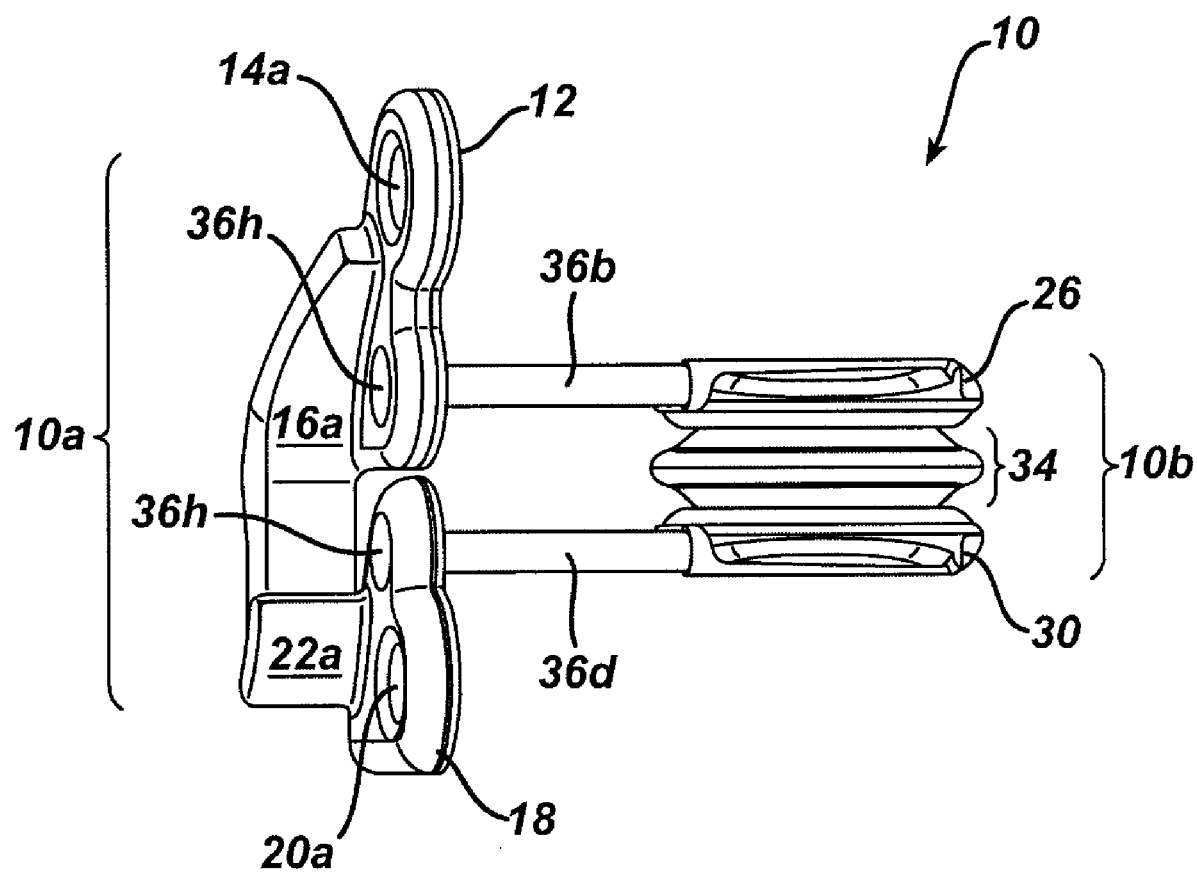
FIG. 8 is a side view of the joint replacement system shown in FIG. 1.

The connectors used to mate the first and second members 12, 18 to adjacent vertebrae can have any configuration that allows the facet replacement device 10a to mate with a disc replacement device 10b. In an exemplary embodiment, as shown in FIGS. 1 and 7, each connector 36a, 36b, 36c, 36d is in the form of an elongate member having a head (36h is shown in FIGS. 7 and 8) formed on one end thereof for seating within one of the openings 19a, 19b, 27a, 27b formed in the first and second members 12, 18, and having an elongate shaft with threads formed on a portion thereof for mating with corresponding threads formed on the disc replacement device 10b, discussed in more detail below. While the connector heads can have a variety of configurations, in one embodiment the heads can be polyaxial to allow the connectors 36a, 36b, 36c, 36d to pivotally move with respect to the first and second members 12, 18.

A person skilled in the art will appreciate that the connectors 36a, 36b, 36c, 36d can have a variety of other configurations. For example, in one embodiment the connectors can be flexible to provide an elastically deformable connection between the facet replacement device 10a and the disc replacement device 10b. Suitable flexible and/or elastic materials include, by way of non-limiting example, polyetheretherketone (PEEK), nylon, polyethylene, titanium, Nitinol, polypropylene, polyurethane, silicone, and stainless steel. In other embodiments, the connectors can be integrally formed with the first and second members 12, 18 or they can be fixedly but rotatably mated to the first and second members 12, 18. The connectors could also be in the form of springs or other flexible members that could allow relative motion between the first and second members 12, 18. Moreover, a variety of other mating techniques can be used to attach one or both of the first and second members 12, 18 to a disc replacement device 10b including, by way of non-limiting example, a snap-fit, an interference fit, a magnetic engagement, etc.

Figure 6A:
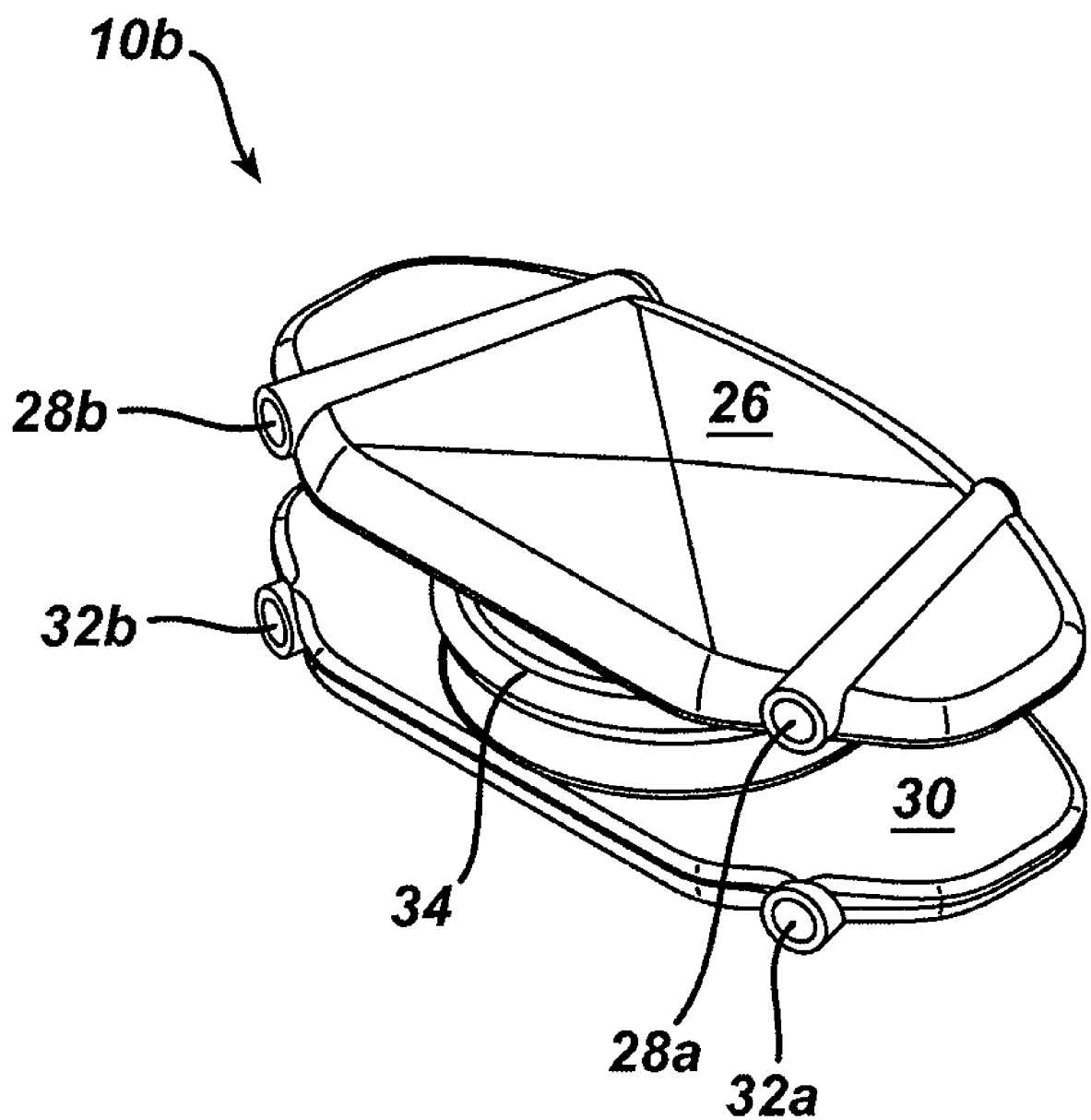
FIG. 6A is a posterior perspective view of the disc replacement component of the joint replacement system shown in FIG. 1.
Figure 6B:
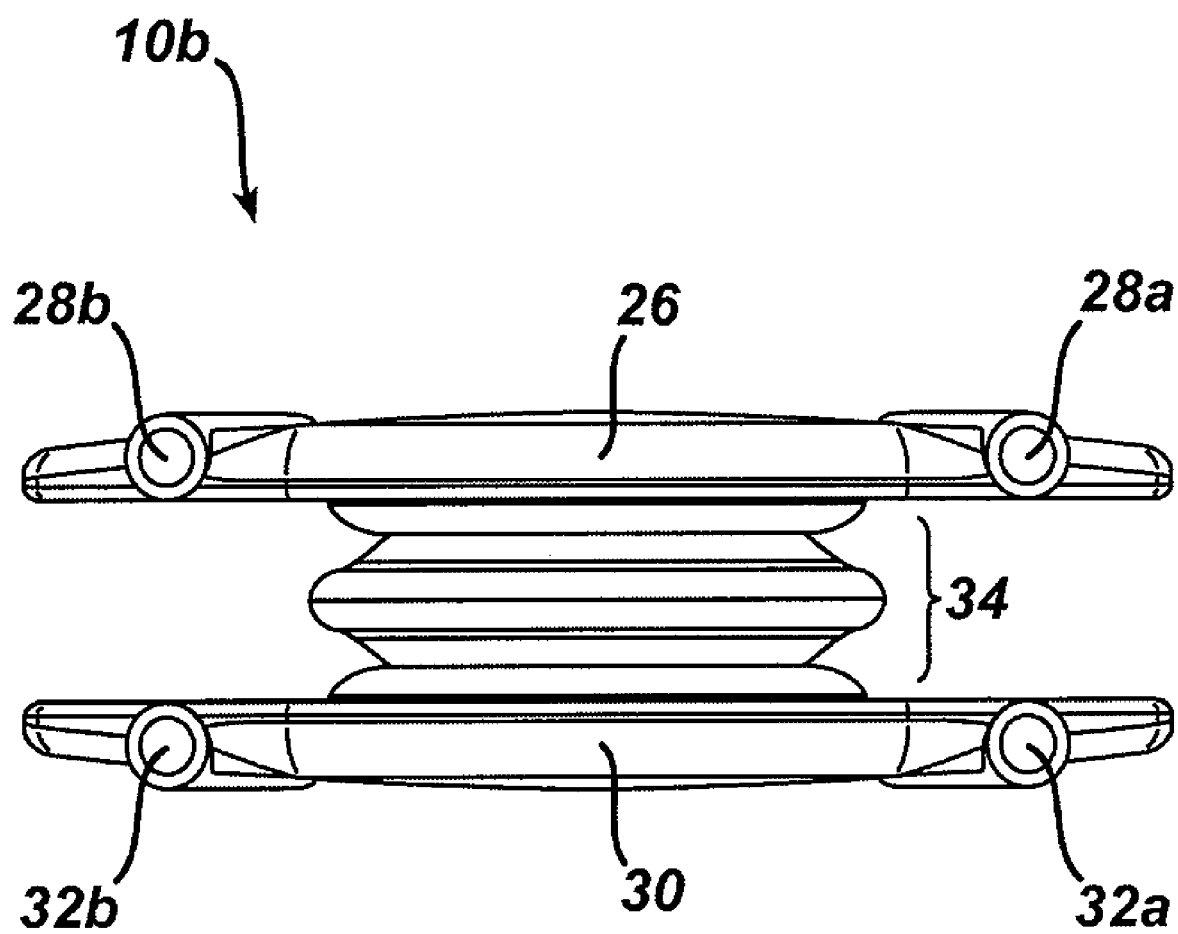
FIG. 6B is a posterior view of the disc replacement component shown in FIG. 6A.

FIGS. 6A-6B show one exemplary embodiment of a disc replacement device 10b that can be used with the facet replacement device 10a. As shown, the disc replacement device 10b has superior and inferior endplate members 26, 30 with a core 34 disposed therebetween. While the endplate members 26, 30 can have a variety of configurations, in the exemplary embodiment the superior endplate member 26 is adapted to be positioned adjacent to an endplate of the superior vertebra, and the inferior endplate member 30 is adapted to be positioned adjacent to an endplate of the inferior vertebra. Both the inner and the outer surfaces of the endplate members 26, 30 can be configured to complement the shape of the vertebral endplates and the core 34, respectively. For example, the outer surfaces of the endplate members 26, 30 can be curved to complement the curve of the vertebral endplates, and the inner surfaces of the endplate members 26, 30 can be concave to complement the convex shape of the core 34. The core 34 can also have any configuration, but in one exemplary embodiment it is substantially disc-shaped with substantially convex superior and inferior surfaces that are adapted to be received within the corresponding substantially concave inner surfaces of the endplate members 26, 30. As a result, the core 34 can pivot relative to the endplate members 26, 30 to allow movement of the adjacent vertebrae relative to one another. One exemplary disc replacement device is the Charité™ Artificial Disc available from DePuy Spine, Inc. The exemplary embodiment shown in FIGS. 1 and 6A-8 differs from the Charite Artificial Disc in that it is smaller, thereby allowing posterior insertion; furthermore, this smaller disc replacement member has mating features for attachment to the facet replacement member(s), as described below. Alternate embodiments of the disc replacement member include, by way of non-limiting example, configurations of one or more components.

As previously indicated, the first and second members 12, 18 of the facet replacement device 10a can be adapted to mate to the disc replacement device 10b. Accordingly, the disc replacement device 10b can include one or more mating features formed thereon to facilitate mating thereof to the first and second members 12, 18. While the mating feature(s) will vary depending upon the configuration of the connector element used to mate the facet replacement device 10a to the disc replacement device 10b, in the illustrated exemplary embodiment, each endplate member 26, 30 includes opposed bores 28a, 28b, 32a, 32b formed thereon for receiving a connector 36a, 36b, 36c, 36d. In the exemplary embodiment, the bores 28a, 28b, 32a, 32b are formed between the inner and outer surfaces of each endplate member 26, 30. Where the endplate member 26, 30 has a width that is less than a width of the connector 36a, 36b, 36c, 36d being used, the region of the endplate member 26, 30 surrounding the bores 28a, 28b, 32a, 32b can protrude above the inner and/or outer surfaces of the endplate members 26, 30. Each bore 28a, 28b, 32a, 32b can also include threads formed therein for mating with corresponding threads formed on the connectors 36a, 36b, 36c, 36d. The bores 28a, 28b, 32a, 32b can, however, utilize a variety of other mating techniques depending on the configuration of the connector, as previously discussed.

In another exemplary embodiment, the facet replacement component 10a and/or the disc replacement component 10b can be provided as a kit. For example, the kit can include multiple facet replacement components 10a that vary with respect to size and configuration. In particular, each facet replacement component 10a can have a different bearing surface angle to allow the surgeon to select a replacement component 10a that limits movement of the adjacent vertebrae as desired. Similarly, the kit can include multiple disc replacement components 10b that vary with respect to size and configuration to allow the surgeon to select endplate members that match the endplates of the patient's vertebrae, and a core that has the appropriate height etc.

Exemplary methods for stabilizing the posterior elements of the spine are also provided. While facet replacement device 10a and disc replacement device 10b are used to describe certain exemplary methods, a person skilled in the art will appreciate that the method can vary depending on the configuration of each device and that a variety of other devices can be used. Moreover, the methods can be performed in any order.

In one exemplary embodiment, a discectomy and facetectomy is performed with a posterior surgical approach using techniques known in the art, and the disc replacement device 10b is positioned between the adjacent vertebrae. In particular, the superior endplate member 26 is positioned adjacent to the endplate of the superior vertebra, and the inferior endplate member 30 is positioned adjacent to the endplate of the inferior vertebra. In one exemplary embodiment, the disc replacement device 10b is sized similar to a TLIF cage so that it can be delivered using an entirely posterior surgical approach.

Figure 9A:
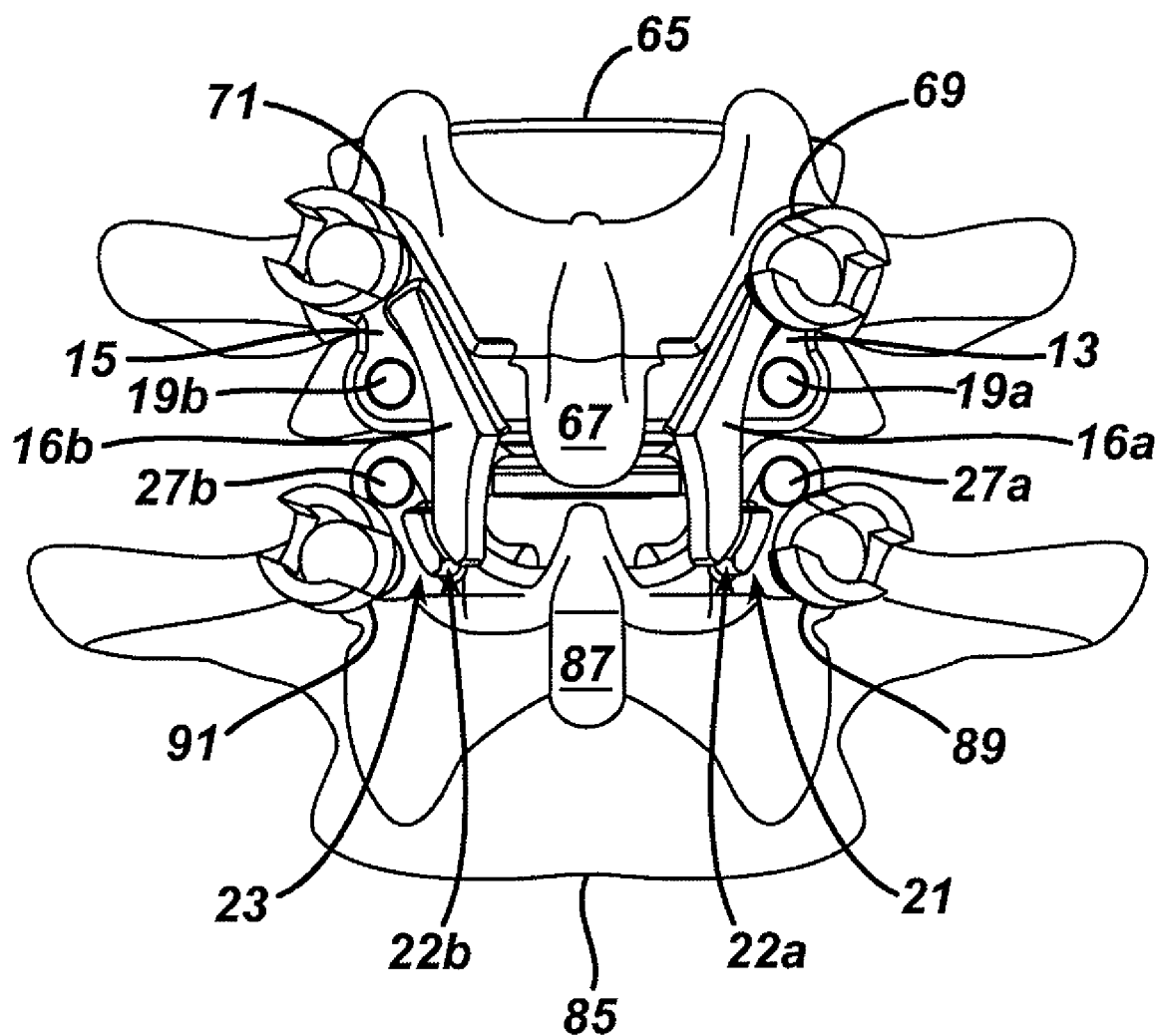
FIG. 9A is a posterior view of the device shown in FIG. 1 coupled to adjacent vertebrae.
Figure 9B:
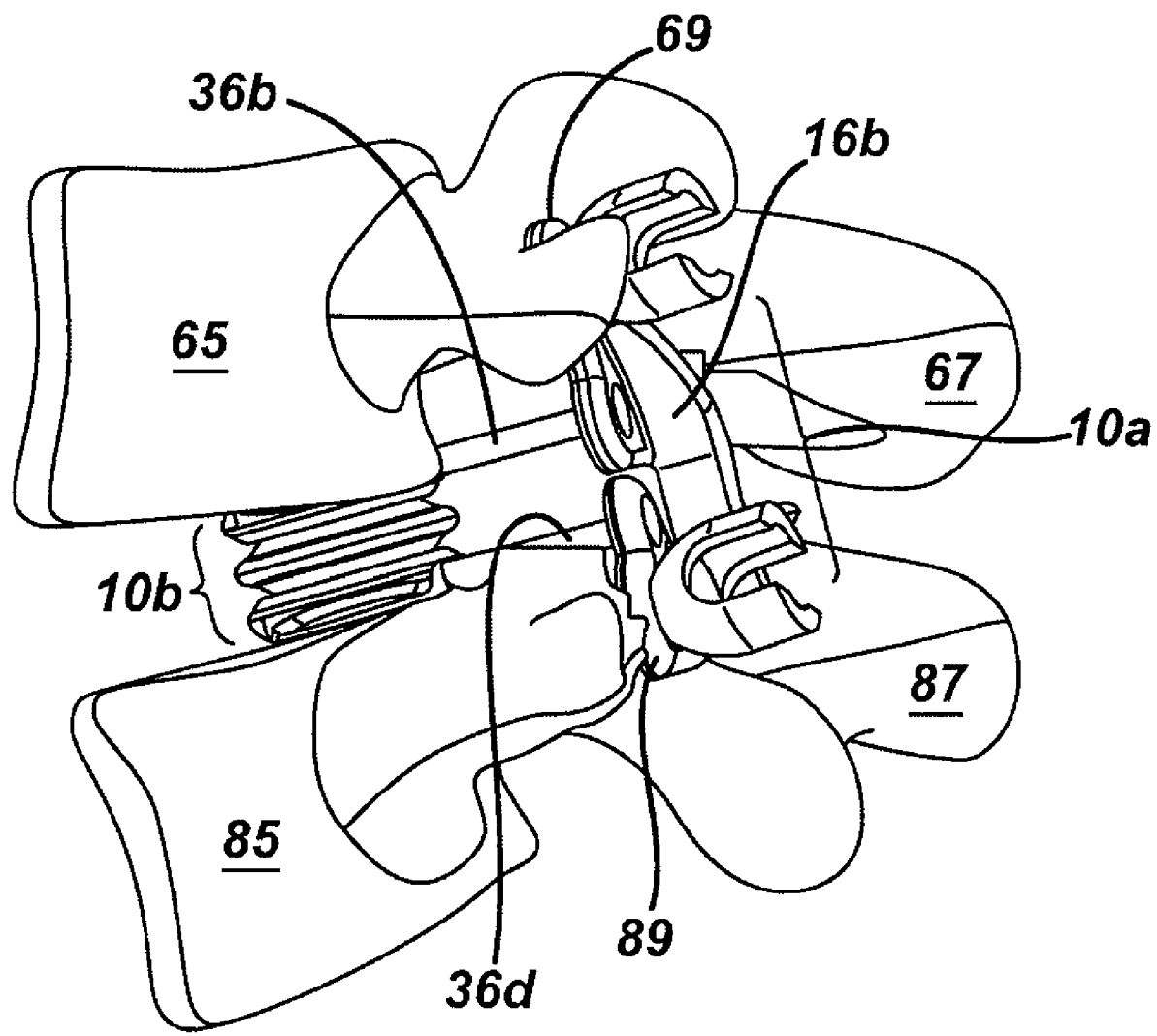
FIG. 9B is a side view of the device shown in FIG. 1 coupled to adjacent vertebrae.

The facet replacement component 10a can then be coupled to the adjacent vertebrae, as shown in FIGS. 9A-9B. In particular, and referring to FIG. 9A, the first member 12 can be positioned on the superior vertebra 65 such that the central portion 17 is positioned inferior to the spinous process 67 and the wing-shaped portions 13, 15 extend in a superior direction on opposed sides of the spinous process 67 and toward the pedicles 69, 71. A bone screw can then be inserted through the thru-bores 14a, 14b in the wing-shaped portions 13, 15 of the first member 12 to attach the first member 12 to the pedicles 69, 71 of the superior vertebra 65. The second member 18 can be positioned on the inferior vertebra 85 such that the central portion 25 is positioned superior to the spinous process 87 and the wing-shaped portions 21, 23 extend toward the pedicles 89, 91 of the inferior vertebra 85. A bone screw can then be inserted through the thru-bores 20a, 20b in the wing-shaped portions 21, 23 to attach the second member 18 to the inferior vertebra 85. While the first and second members 12, 18 can be implanted in any order, in one exemplary embodiment the second member 18 is positioned as desired and the first member 12 is then positioned as necessary based on the positioning of the second member 18.

While FIGS. 9A-9B illustrate the device implanted on adjacent superior and inferior vertebrae with the spinous process still substantially intact, one skilled in the art will appreciate that either all or a portion of the spinous process can be removed, and the device will still function in the same manner as discussed herein.

Referring back to FIG. 7, before or more preferably after the first and second members 12, 18 are attached to the superior and inferior vertebrae, the first and second members 12, 18 can be attached to the disc replacement component 10b using at least one connector 36a, 36b, 36c, 36d. In the illustrated embodiment, two connectors 36a, 36b are inserted through the two openings (shown in FIG. 4 as 19a, 19b) formed in the first member 12, and two connectors 36c, 36d are inserted through the two openings (shown in FIG. 4 as 27a, 27b) formed in the second member 18. The connectors 36a, 36b, 36c, 36d are inserted into corresponding bores 28a, 28b, 32a, 32b formed in the superior and inferior endplate members 26, 30 of the disc replacement component 10b to engage the disc replacement component 10b. Once connected, the facet replacement component 10a in combination with the disc replacement component 10b is effective to control movement of the adjacent vertebrae relative to one another. A person skilled in the art will appreciate that the disc replacement component 10b can also be adapted to be implanted on an anterior side of the vertebrae.

The connectors 36a, 36b, 36c, 36d can also be used to adjust a position of the disc replacement component 10b between the adjacent vertebrae. In particular, once the heads (only head 36h is shown in FIG. 7) of the connectors 36a, 36b, 36c, 36d are seated within the openings 19a, 19b, 27a, 27b, additional rotation of the threaded connectors 36a, 36b, 36c, 36d will pull the endplate members 26, 30, and thus the disc replacement component 10b, toward the facet replacement component 10a. Alternatively, counter-rotation of the threaded connectors 36a, 36b, 36c, 36d will push the disc replacement component 10b away from the facet replacement component 10a. As a result, the disc replacement component 10b can be positioned as desired, especially if the positioning adjustment is performed under fluoroscopic guidance. For posteriorly inserted embodiments of the disc replacement device 10b, this positional control would serve two key functions: the risk of subsidence would be minimized by positioning the disc replacement device posteriorly over the strongest bone of the vertebral endplate; and the location of the center of rotation could be optimized by placing it posteriorly in the disc space. In other embodiments, the disc replacement component can be in the form of a wedge, such that movement of the disc replacement component in a posterior direction will increase the angle between the endplates of the adjacent vertebrae and increase lordosis to match the patient's anatomy.

The position of the disc replacement component 10b can also be adjusted externally once the surgery is completed, e.g., to perform a post-surgical revision. For example, the connectors 36a, 36b, 36c, 36d can include magnetic heads formed thereon that allow the connectors 36a, 36b, 36c, 36d to be rotated using an external magnetic field. This is preferably performed using an imaging means, such as fluoroscopy, to view the disc replacement component 10b and obtain the desired position. A person skilled in the art will also appreciate that the connectors 36a, 36b, 36c, 36d can have a configuration that allows them to be used to move the disc replacement component 10b away from the facet replacement component 10a. For example, the connectors 36a, 36b, 36c, 36d can be fixedly but rotatably coupled to the first and second members 12, 18 and they can have a length that is adapted to move the disc replacement component 10b when the connectors 36a, 36b, 36c, 36d are mated thereto.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. A method for stabilizing the posterior elements in adjacent vertebrae, comprising:
   positioning the majority of a plate portion of superior and inferior facet replacement members on a posterior surface of adjacent superior and inferior vertebrae;
   the superior facet replacement member having a first protrusion;
   the inferior facet replacement member having a second protrusion;
   coupling the superior and inferior facet replacement members to the adjacent superior and inferior vertebrae such that the first protrusion bears against the second protrusion such that the superior and inferior facet replacement members articulate with one another to control movement of the first and second vertebrae relative to one another;
   coupling at least one of the superior and inferior facet replacement members to at least one connector; and
   directly coupling the at least one connector to a disc replacement member disposed between the adjacent superior and inferior vertebrae.

2. The method of claim 1, wherein the superior and inferior facet replacement members articulate with one another as the superior and inferior vertebrae move relative to one another.

3. The method of claim 1, wherein coupling the superior and inferior replacement members to adjacent superior and inferior vertebrae comprises positioning the superior replacement member on a posterior surface of the superior vertebra, positioning the inferior replacement member on a posterior surface of the inferior vertebra, and mating the superior and inferior replacement members to the superior and inferior vertebrae.

4. The method of claim 3, wherein the superior and inferior replacement members each include a central portion and wing-shaped portions formed on opposed ends of the central portion, the central portion of the superior replacement member being positioned inferior to a spinous process of the superior vertebra, and the central portion of the inferior replacement member being positioned superior to a spinous process on the inferior vertebra.

5. The method of claim 4, wherein the wing-shaped portions on the superior replacement member are mated to pedicles of the superior vertebra, and the wing-shaped portions on the inferior replacement member are mated to pedicles of the inferior vertebra.

6. The method of claim 3, wherein mating the superior and inferior replacement members to the superior and inferior vertebrae comprises inserting a fastening element through at least one thru-bore formed in the superior and inferior replacement members.

7. The method of claim 6, wherein the fastening element comprises a bone screw, and the at least one thru-bore is polyaxial.

8. The method of claim 1, wherein coupling at least one of the superior and inferior facet replacement members to at least one connector comprises inserting the at least one connector through at least one thru-bore formed in at least one of the superior and inferior facet replacement members, and mating a portion of the at least one connector to the disc replacement member.

9. The method of claim 8, further comprising using the at least one connector to adjust a position of the disc replacement member relative to the superior and inferior vertebrae to position the disc replacement member at a desired location.

10. The method of claim 9, wherein the at least one connector is threadably mated to the disc replacement member, and adjusting the position of the disc replacement member comprises rotating the at least one connector.

11. The method of claim 10, wherein the at least one connector is rotated using a magnetic field.

12. A method of replacing the spinal three joint complex, comprising:
    replacing a disc disposed between superior and inferior vertebrae with a disc replacement member;
    positioning the majority of a plate portion of superior and inferior facet replacement members on a posterior surface of adjacent superior and inferior vertebrae;
    the superior facet replacement members having first protrusions;
    the inferior facet replacement members having second protrusions;
    attaching opposed lateral portions of the superior facet replacement member to opposed pedicles on the superior vertebra and
    attaching opposed lateral portions of the inferior facet replacement member to opposed pedicles on the inferior vertebra such that the first protrusions bear against the second protrusions such that the superior and inferior facet replacement members articulate with one another to control movement of the first and second vertebrae relative to one another;
    coupling at least one of the superior and inferior facet replacement members to at least one connector; and
    directly coupling the at least one connector to the disc replacement member.

13. The method of claim 12, wherein the superior facet replacement member includes a central portion that extends between the opposed lateral portions and that is positioned inferior to a spinous process on the superior vertebra, and wherein the inferior facet replacement member includes a central portion that extends between the opposed lateral portions and that is positioned superior to a spinous process on the inferior vertebra.

14. The method of claim 12, wherein the superior and inferior facet replacement members are coupled to superior and inferior portions of the disc replacement member.

15. The method of claim 12, wherein coupling at least one of the superior and inferior facet replacement members to the at least one connector comprises inserting the at least one connector through at least one bore formed in at least one of the superior and inferior facet replacement members, and mating a portion of the at least one connector to the disc replacement member.

16. The method of claim 15, wherein the at least one connector is threadably mated to the disc replacement member and the at least one bore is polyaxial.

17. The method of claim 16, further comprising rotating the at least one connector to adjust a position of the disc replacement member between the superior and inferior vertebrae.

18. The method of claim 12, wherein the superior and inferior replacement members articulate relative to one another as the superior and inferior vertebrae move relative to one another.

19. The method of claim 12, wherein the superior and inferior replacement members are adapted to allow flexion and limit extension of the superior and inferior vertebrae relative to one another.

20. The method of claim 19, wherein the superior and inferior replacement members are further adapted to limit lateral bending and axial rotation of the superior and inferior vertebrae relative to one another.

* * * * *